United States Patent [19]

Aretz et al.

[11] Patent Number: 5,260,206
[45] Date of Patent: Nov. 9, 1993

[54] ENZYMES FOR BREAKING DOWN MOENOMYCINS

[75] Inventors: Werner Aretz, Königstein/Taunus; Dirk Böttger, Hünstetten; Gerhard Seibert, Darmstadt; Alois Tumulka, Königstein/Taunus; Peter Welzel; Kurt Hobert, both of Bochum, all of Fed. Rep. of Germany

[73] Assignee: Hoechst Aktiengesellschaft, Frankfurt am Main, Fed. Rep. of Germany

[21] Appl. No.: 938,599

[22] Filed: Sep. 3, 1992

Related U.S. Application Data

[63] Continuation-in-part of Ser. No. 762,262, Sep. 20, 1991, abandoned, which is a continuation of Ser. No. 711,708, Jun. 7, 1991, which is a continuation of Ser. No. 395,790, Aug. 18, 1989.

[30] Foreign Application Priority Data

Aug. 20, 1988 [DE] Fed. Rep. of Germany ....... 3828337

[51] Int. Cl.⁵ .................. C12N 1/20; C12N 9/14; C12P 19/44; C12P 7/42
[52] U.S. Cl. .................... 435/195; 435/194; 435/196; 435/199; 435/252.5; 435/832
[58] Field of Search ............. 435/21, 194, 195, 196, 435/199, 832, 252.5

[56] References Cited

U.S. PATENT DOCUMENTS

| | | | |
|---|---|---|---|
| 4,168,203 | 9/1979 | Takahashi et al. | 435/21 |
| 4,684,626 | 8/1987 | Welzel et al. | |
| 4,816,563 | 3/1989 | Wilson et al. | 435/70.4 |
| 4,855,237 | 8/1989 | Moringa et al. | 435/172.3 |
| 4,886,747 | 12/1989 | Derynck et al. | 435/172.1 |
| 4,921,801 | 5/1990 | Rao et al. | 435/252.33 |
| 4,940,661 | 7/1990 | Etcheverry et al. | 435/256 |

OTHER PUBLICATIONS

A. L. Lehninger, Biochemistry, Second Edition, pp. 195-197 (1970).
G. Huber, Antibiotics, 1:135-153 (1979).
Fehlhaber et al., "Moenomycin A: A Structural Revision And New Structure-Activity Relations," Tetrahedron, 46(5):1557-1568 (1990).
A. L. Lehninger, Biochemistry, Second Edition, pp. 195-197 (1970).
Takahashi et al., "Structure of Pholipomycin," Tetrahedron 24(5):499-502 (1983).

*Primary Examiner*—Herbert J. Lilling
*Attorney, Agent, or Firm*—Finnegan, Henderson, Farabow, Garrett & Dunner

[57] ABSTRACT

A new Bacillus species and the appropriate enzymes obtained therefrom can be used to break down phosphoglycolipid antibiotics. The breakdown products of moenomycins display antibiotic activity or can be used as building blocks for the synthetic preparation of transglycosylas inhibitors.

2 Claims, 2 Drawing Sheets

ENZYMES FOR BREAKING DOWN MOENOMYCINS

This application is a continuation-in-part of application Ser. No. 07/762,262, filed Sep. 20, 1991, abandoned, which is a continuation of application Ser. No. 07/711,708, filed Jun. 7, 1991, which is a continuation of Ser. No. 07/395,790, filed Aug. 18, 1989.

Moenomycin A (FIG. 1) is the main component of Flavomycin ® which is used in livestock nutrition. Like other known phosphoglycolipid antibiotics it inhibits the biosynthesis of the peptidoglycan framework of the bacterial cell wall. Closer investigations showed that the transglycosylation reaction of the penicillin-binding protein 1b of *E. coli* is inhibited by these substances [Huber G., Antibiotics, V-1,, pages 135 to 153 (1979)]. Attempts at specific enzymatic or microbial breakdown of phosphoglycolipid antibiotics have hitherto failed.

Surprisingly, a new Bacillus species which is able to cleave the phosphoglycolipid antibiotics to defined end products has now been isolated from a contaminated fermenter for the preparation of flavomycin using Streptomyces ghanaensis. These end products have antibiotic activity or can be used as building blocks in the synthesis of new transglycosylase inhibitors.

Hence the invention relates to:
1. Bacillus spec. DSM 4675 and the variants and mutants thereof.
2. The cleavage product of moenomycin A with the formula I
3. The cleavage product of the phosphoglycolipid antibiotics with the general formula $$R^1O-CH_2-CH-OR^2 \atop |\atop COOH \qquad (II)$$

in which $R^1$ is hydrogen or a phosphono group [$-PO(OH)_2$] and $R^2$ is a ($C_5$ to $C_{55}$)-alkyl group which can be branched or unbranched, saturated or unsaturated.

4. The enzymes with whose aid the phosphoglycolipid antibiotics can be cleaved at the phosphoglycosidic linkage, or the cleavage products specified under 3. can be cleaved at the monophosphate ester linkage.
5. A process for the preparation of the breakdown products specified under 2. and 3., which comprises incubating phosphoglycolipid antibiotics with Bacillus spec. DSM 4675.
6. The use of the substances specified under 2. and 3. as building block for the synthetic preparation of transglycosylase inhibitors or as substance having antibiotic activity.

The invention will be described in detail hereinafter, especially in the preferred embodiments. It is furthermore defined in the claims.

Bacillus spec. was deposited with the number DSM 4675 under the provisions of the Budapest Treaty at the Deutsche Sammlung von Mikroorganismen und Zellkulturen GmbH (German Microorganism and Cell Culture Collection) in Braunschweig, FRG, on Jun. 23, 1988. The characteristics of the strain may be said to be the following:

1. Taxonomic properties of Bacillus sp. DSM 4675
    A) Morphology
        motile rods; up to 5 μm long; some in short chains
        terminal spore; sporangium swollen
        Gram-positive.
    B) Growth on various media (28° C.; 48 hours)
        1. Antibiotic medium 3 (Difco)
            rough, lobed colonies of diameter 1-2 mm 2. Luria broth (Bacto tryptone 10 g/l Bacto yeast 5 g/l NaCl 5 g/l
smooth, glossy round colonies of diameter 2-3 mm; opaque
3. Nutrient broth (Difco)
white, glossy colonies with irregular margin
4. Christensen urea agar (Difco)
growth positive
5. McConkey agar (Difco)
growth positive
6. BROLAC agar (lactose) (Difco)
growth positive
7. Simmons citrate agar (Difco)
growth negative
8. . No growth in the presence of 7 or 10% NaCl in a peptone/meat extract medium (Difco)

| C) Physiological properties | |
|---|---|
| 1. Oxidase | + |
| 2. Catalase | + |
| 3. Hemolysis | − |
| 4. Aminopeptidase | − |
| 5. Nitrate reduction | − |
| 6. Phenylalanine deaminase | − |
| 7. Growth at | |
| 30° C. | + |
| 40° C. | + |
| 50° C. | + |
| 8. Anaerobic growth | |
| solid | − |
| liquid | − |
| 9. Gas formation from glucose | − |
| 10. Indole formation | − |
| 11. Arginine dihydrase | − |
| 12. Urea breakdown | − |
| 13. Esculin hydrolysis | + |
| 14. Gelatin breakdown | − |
| 15. β-Galactosidase | + |
| 16. Lysine decarboxylase | − |
| 17. Ornithine decarboxylase | − |
| 18. H$_2$S production | − |
| 19. Tryptophan deaminase | − |
| 20. Alkal. phosphatase | − |
| 21. Voges-Proskauer reaction | − |

| D) Fermentation of carbohydrates | | |
|---|---|---|
| C source | Assimilation | Acid formation |
| Adipate | − | |
| Adonitol | − | |
| Arabinose | + | + |
| Caprate | − | |
| Citrate | − | |
| Dulcitol | − | |
| Fructose | + | + |
| Galactose | − | |
| Gluconate | + | |
| Glucose | + | + |
| Inositol | − | |
| Lactose | + | + |
| Malate | − | |
| Malonate | − | |
| Maltose | + | + |
| Mannitol | + | + |
| Mannose | + | + |
| Melibiose | + | + |
| Phenylacetate | − | |
| Raffinose | + | + |
| Rhamnose | − | |
| Sucrose | + | + |
| Salicin | − | |
| Sorbitol | − | |
| Trehalose | + | + |
| Xylitol | − | − |
| Xylose | + | + |
| N-Acetyl-glucosamine | − | + |

Taking account of taxonomic features and with the aid of "Bergey's Manual of Systematic Bacteriology" (Vol. 2, Williams and Wilkins publ., Baltimore, 1986) the strain can be assigned to the genus Bacillus. To determine the species, parallel comparative examinations of type cultures of Bacillus macerans, circulans, lentus, alcalophilus, stearothermophilus, licheniformis, polymyxa and fastidiosus were carried out. All the comparison strains showed distinct differences from Bacillus spec. DSM 4675. Nor were any of these strains able to break down phosphoglycolipid antibiotics, especially moenomycin A. The conclusion to be drawn from this is that the strain DSM 4675 is a new species.

The invention also relates in each case to the mutants and variants which, as is known, may arise spontaneously or be generated by treatment with physical agents, for example irradiation, such as ultraviolet or X-rays, or with chemical mutagens such as, for example, ethyl methanesulfonate(EMS), N-methyl-N'-nitro-N-nitrosoguanidine (MNNG) or 2-hydroxy-4-methoxybenzophenone (MOB).

Suitable and preferred as carbon source for the aerobic fermentation of Bacillus spec. DSM 4675 are assimilable carbohydrates and sugar alcohols, such as glucose, lactose or mannitol, as well as carbohydrate-containing natural products such as malt extract. Suitable and preferred nitrogen-containing nutrients are: amino acids, peptides and proteins, as well as the breakdown products thereof, such as peptone or tryptone, furthermore meat extracts, milled seeds, for example of corn, beans, soybean or the cotton plant, disillation residues from the production of alcohol, meat meals or yeast extracts, as well as ammonium salts and nitrates. The nutrient solution may additionally contain, for example, chlorides, carbonates, sulfates or phosphates of the alkali metals or alkaline earth metals, iron, zinc and manganese as additional inorganic salts.

The growth of the microorganism and the formation of the enzymes necessary for the breakdown reactions according to the invention is particularly good in a nutrient medium containing corn starch, soybean meal, sucrose, glycerol, peptone and/or corn steep as carbon and nitrogen sources.

The fermentation is carried out aerobically, that is to say, for example, submerged with shaking or stirring in shaken flasks or fermenters, where appropriate introducing air or oxygen. The fermentation can take place in a temperature range from approximately room temperature to 50° C., preferably at about 35° to 37° C. The culturing time is generally 24 to 48 hours.

The cultures of Bacillus DSM 4675 obtained in this way, or preparations thereof, can be used to cleave the phosphoglycolipid antibiotics. These include, in particular, the antibiotics of the moenomycin group, for example pholipomycin[1], the prasinomycins[2], the diumycins (macarbomycins)[3] esanchomycin, prenomycin and teichomycin, and other structurally related substances which have a correspondingly functionalized phosphoglyceric acid

[1] S. Takahashi et al., Tetrahedron Lett. 1983, 499
[2] F. L. Weisenborn et al., Nature 213, 1092 (1967)
[3] S. Takahashi et al., J. Antibiot. 26, 542 (1973).

The enzymes are particularly preferably used to break down the moenomycins, for example Flavomycin.

When Bacillus cells are used it is advantageous to permeabilize the latter, for example with cetyltrimethylammonium salts. It is likewise possible to use protein isolates from the Bacillus cells, or enzyme extracts which have been partially enriched, for example, by salting-out or chromatography or, of course, the purified enzyme. It is furthermore possible to employ the enzyme and cells in free or immobilized form.

The enzymatic breakdown is depicted in the following diagram using moenomycin A as an example.

-continued
Enzymatic breakdown of moenomycin A

MA

It is evident from this diagram that two enzymes are needed to prepare the cleavage products. An enzyme, which the inventors have called moenomycinase, is required to cleave the phosphoglycosidic linkage. Moenomycinase is associated with the cytoplasmic membrane of Bacillus spec. DSM 4675 and can be obtained from the microorganism by enzyme isolation methods known per se. For example, moenomycinase bound to membranes of Bacillus spec. DSM 4675 can be solubilized with the detergent Triton X-100 (1–3%) as described in Example 2A. Moenomycinase can also be isolated without the use of detergent by more extensive ultrasound sonication. For example, cells suspended in buffer (20 mM potassium phosphate, pH 8.0, with 0.1 mM CoCl$_2$) were sonicated for 1–2 minutes. After centrifugation at 20 min × 20,000 g, 50–60% of the enzyme activity was found in the supernatant. Alternatively, some activity can be solubilized with cetyltrimethylammonium salts. For example, when cells were incubated (1 g/2 ml) in 0.1% cetyltrimethylammonium salts (0.1%), 10% of the enzyme activity was found in the supernatant after centrifugation for 20 min × 20,000 g.

Figure 1:
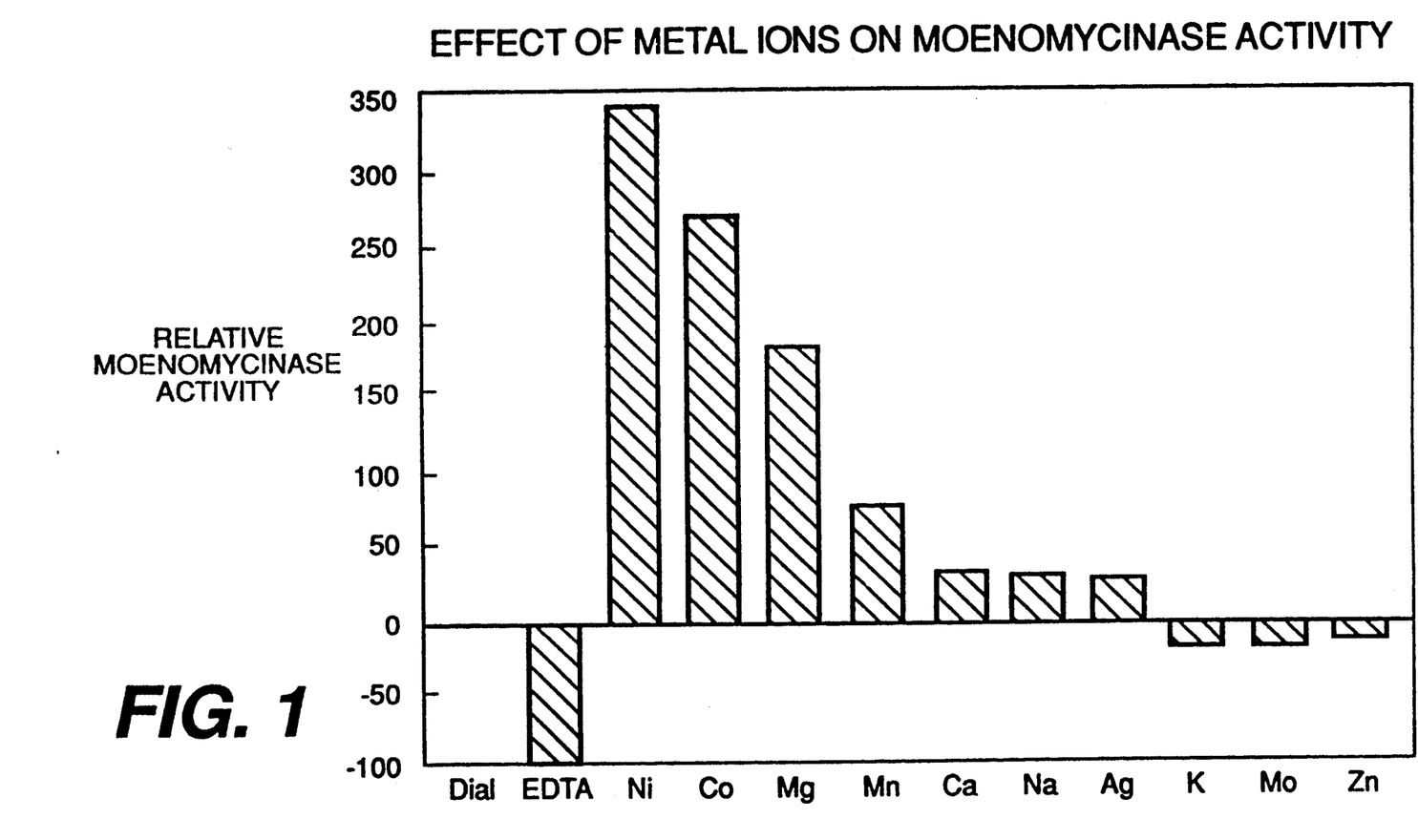
FIG. 1. Effect of Metal Ions on Moenomycinase Activity. Partially purified moenomycinase was dialyzed for 24 hours. The dialyzed moenomycinase was incubated with moenomycin A (6 mg/ml) in 100 mM potassium phosphate buffer, pH 8.0, for 31 hours with the addition of metal ions (0.5 or 1.0 mM, except $K^+=20$ mM) or EDTA (10 mM). Enzyme activity was measured by determining the amount of MC formed using TLC and UV analysis as described in Example 3. The TLC plates were scanned at a wavelength of 254 nm using a DESAGA Chromatogram Densitometer CD50. Enzyme activity is expressed relative to the activity of the dialyzed preparation ("Dial").

The molecular weight of moenomycinase is 230,000 ± 10,000 Dalton. Moenomycinase is activated by Co$^{++}$, Ni$^{++}$, Mn$^{++}$, Ca$^{++}$ and Mg$^{++}$, and can be inhibited by formalin, EDTA, Cephalosporin C, and 7-aminocephalosporin acid (7-ACA). FIG. 1 illustrates the effects of metal ions and EDTA on moenomycinase activity.

Moenomycinase has a pH optimum of about 8.0–8.5, in particular 8.2–8.3. The temperature optimum of the enzyme is 45°–55° C., in particular 49°–51° C. Moenomycinase has a K$_m$ value for moenomycin A of 4–10 millimolar.

Two cleavage products are obtained. Cleavage product I comprises the sugar component of the phosphoglycolipid antibiotics. Also obtained is the cleavage product with the general formula II

II in which R$^1$ is a phosphono group and R$^2$ is a (C$_5$ to C$_{55}$)-alkyl group, preferably a (C$_{10}$ to C$_{30}$)-alkyl group, in particular a (C$_{20}$ to C$_{25}$)-alkyl, each of which can be branched or unbranched, saturated or unsaturated, preferably branched and unsaturated.

Figure 2:
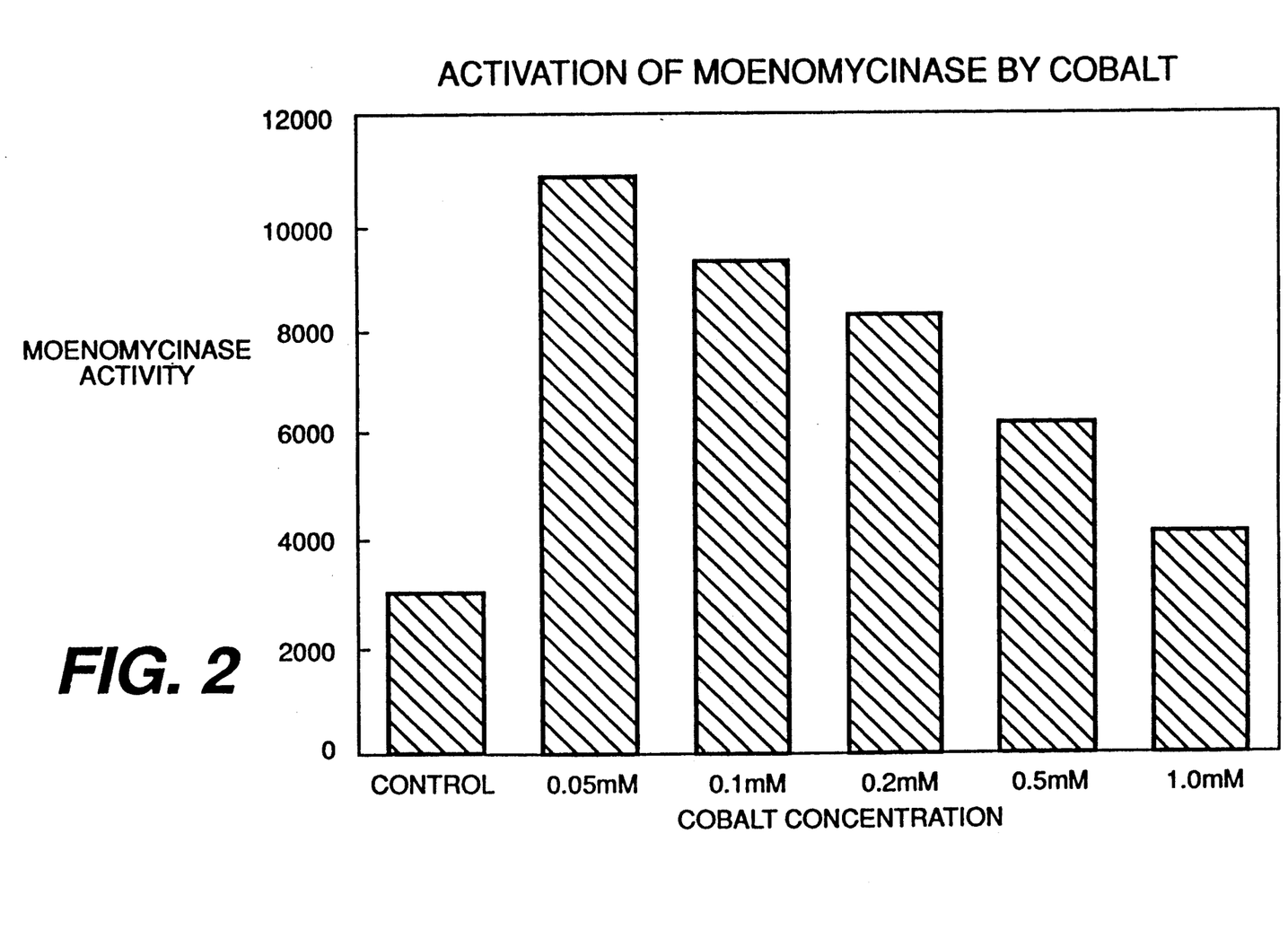
FIG. 2 Activation of Moenomycinase by Cobalt. Purified moenomycinase was incubated with moenomycin A in the present of the indicated concentrations of $Co^{++}$. Enzyme activity was measured by determining the amount of MB formed using TLC and UV analysis as described in FIG. 1.

Moenomycins are preferably employed as substrates, so that the resulting cleavage products are the substances corresponding to the compound MC, as well as the compounds MB and MA (see formula diagram). Moenomycinase is activated by metal ions such as Co$^{++}$, Ni$^{++}$, Mn$^{++}$ and Mg$^{++}$ (0.05–1.0 mM). See FIG. 1. Although greatest activation is seen with Ni$^{++}$, the currently preferred ion for activation of moenomycinase for commercial development is Co$^{++}$ (0.10 mM). FIG. 2 shows the effect of Co$^{++}$ concentration on moenomycinase activity.

Another enzyme is required for the dephosphorylation of the phosphoglyceric acid lipid, which is obtained by incubation with moenomycinase, of the general formula II in which R$^1$ is hydrogen, and can also be obtained from the microorganism according to the invention. The inventors have called this enzyme MBase. MBase can likewise be isolated from the microorganism by methods known per se. For example, the cells are disrupted with ultrasound, and the resulting crude extract is further enriched either by ammonium sulfate fractionation (25–55% saturation) or ultracentrifugation. This is followed by dialysis. The moenomycinase and MBase are finally separated by chromatography.

The MBase is increasingly inactivated at temperatures above 37° C. as well as when the pH falls in the acid pH range below pH 5.

The cleavage of the moenomycins, as well as of the phosphoglycolipid antibiotics can, as already mentioned, be carried out with whole cells or enzyme isolates.

The reaction is generally carried out in aqueous medium at a pH of about 5.5–8.5, preferably pH 7–8. The reaction time is generally 5–48 hours, preferably about 24 hours. The reaction temperature can be from 4° to 60° C., preferably 30° to 37° C. The substrate concentration ought to be in the range from 0.1 to 5%, preferably 1 to 2%.

It is still possible to carry out the reaction at temperatures or pH values which are higher or lower than stated. However, the moenomycinase is then less active.

The reaction products resulting from moenomycin A are the substances MB and MC depicted in the diagram. The product MA can be obtained by incubation of MB with MBase at 30° to 37° C., preferably at 35° to 37° C., and pH 5.5 to 8.5, preferably pH 6 to 8, over a period of about 24 hours.

The said reaction products can be used as antibiotic (for example MB) or as building block for the synthesis of transglycosylase inhibitors (for example MA and MC).

The invention is described in more detail by means of examples. Unless stated otherwise, percentage data relate to weight.

EXAMPLE 1

Maintenance of the Bacillus Spec. DSM 4675 Strain

Bacillus spec. DSM 4675 is maintained on the following solid nutrient medium (medium 1):

| | |
|---|---|
| Bacto tryptone (Difco) | 10 g/l |
| Yeast extract (Difco) | 5 g/l |
| NaCl | 5 g/l |
| Agar | 15 g/l |
| pH 7.2 | |

The medium is distributed over test tubes and sterilized at 121° C. for 30 minutes, then cooled, inoculated with the culture and incubated at 37° C. for 2–3 days.

The grown culture is rinsed off to provide the inoculum for the following, moenomycin-containing main culture (medium 2):

| | |
|---|---|
| Corn starch | 40 g/l |
| Soybean meal | 35 g/l |
| Sucrose | 10 g/l |
| $CaCO_3$ | 8 g/l |
| Corn steep | 4 g/l |
| $CoSO_4$ | 20 mg/l |
| ® Genapol (alkyl polyglycol ester | 5 ml/l |
| Moenomycin A | 3 g/l (sterile filtered) |
| pH 7.6 | |

300 ml Erlenmeyer flasks each containing 30 ml of this medium are inoculated and then incubated at 37° C. and 190 rpm for 8–48 hours. Analysis of the culture filtrate by thin-layer chromatography shows that the compounds MA, MB and MC are detectable as cleavage products of moenomycin, and that towards the end of the reaction there has been complete disappearance of the moenomycin employed.

EXAMPLE 2

Preparation of Cell-free Extracts

To prepare cell-free extracts, Bacillus spec. DSM 4675 is cultured in a fermenter. For this, cells are rinsed off the agar plate to provide a 10 ml inoculum for a preculture (500 ml of medium 2 without Flavomycin in a 2 l Erlenmeyer flask) which is then incubated at 37° C. and 190 rpm for 24 hours.

A 12 l laboratory fermenter containing 9 l of medium 3 is used for the main culture stage.

| | |
|---|---|
| Peptone | 12.5 g/l |
| Glycerol | 20.0 tg/l |
| Citrate | 2.0 g/l |
| $K_2HPO_4$ | 1.5 g/l |
| $MgSO_4 \times 7H_2O$ | 0.5 g/l |
| $FeCl_3 \times 6H_2O$ | 0.04 g/l |
| Desmophen (propylene glycol) | 5.0 ml/l |
| pH 6.8 | |

This is inoculated with 500 ml of preculture and incubated at 37° C., 300 rpm and an aeration rate of 0.5 vvm for 24 hours.

The grown culture is centrifuged, and the cell paste is resuspended in potassium phosphate buffer (pH 7.0) 50 mM (1 g of wet cells +2 ml of buffer). The cells are then disrupted with ultrasound, a French Press ® or Dyno Mill ®, and the resulting crude extract is used for the conversion.

In a test mixture containing 100 μl of crude extract, 12 mg of moenymycin and 90 μl of potassium phosphate buffer (pH 8.0) 50 mM there is within 7–24 hours at 37° C. 50% breakdown of the substrate employed. The reaction products found are MA, MB and MC.

EXAMPLE 2A

Isolation of Moenomycinase

Moenomycinase has been isolated from Bacillus spec. DSM 4675 as follows:

Cells grown as in Example 2 were suspended at a concentration of 1 g cells/2 ml in 20 mM potassium phosphate buffer, pH 8.0, containing 0.1 mM $CoCl_2$. The suspended cells were sonicated for 20 seconds. After sonication, the suspension was centrifuged for 20 min×20,000 g. The supernatant was discarded and the pellet resuspended in the same buffer to which has been added 1% Triton X-100 and incubated for 1 hr at room temperature with stirring. The suspension was then centrifuged for 2.5 hrs×100,000 g. After such centrifugation, 90–95% of the moenomycinase activity was found in the supernatant.

Moenomycinase solubilized using Triton X-100, as described above, was further purified by $(NH_4)_2SO_4$ precipitation. As $(NH_4)_2SO_4$ concentration was increased from 0% to 40%, the moenomycinase precipitated at 30–40% and entered a fatty phase that floats above the aqueous phase. The aqueous phase was discarded, and the fatty phase was dissolved in 20 mM Tris HCl buffer, pH 8.0, containing 0.1 mM $CoCl_2$ and 0.1% Triton X-100.

The dissolved enzyme was further purified by chromatography. For anion exchange chromatography, the enzyme was bound to a column of DEAE-52 (Whatman) or MonoQHR-5-5 (Pharmacia) and then eluted with 0.2–1.0M NaCl. Presence of moenomycinase in the fractions was monitored by measuring the conversion of moenomycin A to MC, as described in Example 3, below. Further purification was achieved using hydrophobic chromatography. The enzyme was bound to phenylsepharose (Pharmacia), and was then eluted with 40% methanol. The enzyme was concentrated by ultrafiltration using an ultrafiltration membrane (Millipore) which retains molecules with molecular weights $\geq$ 10,000 Dalton. The moenomycinase was further purified by molecular sieve chromatography using Sephacryl S-200HR (Pharmacia). The enzyme was separated in the Sephacryl chromatography column in 20 mM Tris HCl or potassium phosphate buffer, pH 8.0, containing 0.1 mM $CoCl_2$ and 0.1% Triton X-100 and washed with additional buffer. By comparison with the elution profiles of a series of standard proteins of differing molecular weight, the molecular weight of the moenomycinase was determined to be 230,000±10,000 Dalton. If desired, the purity of the isolated moenomycinase fraction can be checked using SDS gel chromatography.

EXAMPLE 3

Preparative Conversion of Moenomycin A

Preparative conversions are carried out in a 12 l fermenter containing 8.2 l of potassium phosphate buffer (pH 8.0) 50 mM, 800 ml of crude enzyme extract and 100 g of moenomycin A at 37° C. and 100 rpm. The progress of the conversion is followed by TLC. The entire reaction mixture is freeze-dried after 8–48 hours. The moenomycin breakdown is generally 40–60% (UV analysis from the TLC). The resulting reaction products are MA, MB and MC.

EXAMPLE 4

Preparation of the Breakdown Products 100 g of freeze-dried mixture from the enzymatic conversion were taken up in 2 l of water and extracted twice with 2 l of ethyl acetate each time. Centrifugation was necessary for complete phase separation in this case. The combined organic extracts were dried over sodium sulfate, filtered and evaporated to dryness. 0.4 g (0.4%) of a dark brown oil was obtained, and thin-layer chromatography in the system n-butanol/acetic acid/water=3/1/2 on silica gel (Merck 60 F254 aluminum TLC sheets), spraying with molybdatophosphoric acid/cerium(IV) sulfate color reagent (abbreviated to PMS reagent hereinafter), showed that it comprised mainly component MA (Rf value=0.85).

The remaining aqueous phase was then extracted twice with 2 l of n-butanol each time. Once again, centrifugation was necessary for phase separation. The combined butanol phases were then concentrated as far as possible, and the residue was taken up in a little water and finally freeze-dried. 7.4 g (7.4%) of a yellow powder were obtained and were found on examination by thin-layer chromatography (using the abovementioned conditions and the same detection) to comprise mainly the component MB (Rf=0.52).

The aqueous phase from which non-polar substances had been removed in this way was freeze-dried. The amount of residue resulting from this was 76.9 g (76.9% with a total amount of 85%). Thin-layer chromatography showed that this pale yellow powder was composed of a polar main substance, called MC (Rf=0.1), remaining moenomycin A and by-products.

The crude products of components MA, MB and MC obtained in this way were further purified as follows.

EXAMPLE 5 a) Purification of the Breakdown Product MA 400 mg of MA crude product were chromatographed on 120 g of silica gel (Merck 60, 15–40 mcm) which had been adjusted to a pH of 7.5. (The column material had been pretreated in the following way for this purpose: the silica gel was stirred in 500 ml of 2N HCl for one hour, then filtered off with suction and washed to neutrality. The pH was then adjusted to 7.5 with 1N NaOH, and finally washing with 2 l of water and 500 ml of methanol was carried out. The material pretreated in this way was dried and activated at 120° C. overnight.) Chloroform/ethanol=1/1 was used as eluent. The substance was loaded onto the column in 3 ml of solvent mixture, and 216 fractions each of 2.5 ml were collected. Using TLC analysis (TLC plates and detection as in Example 1, solvent system as for column eluent), fractions 115–175 were combined, dried on sodium sulfate and finally evaporated to dryness. 27 mg of spectroscopically pure MA were obtained.

b) Purification of the Breakdown Product MB 3.1 g of MB-containing crude product from the extraction were chromatographed on 500 g of silica gel which had been adjusted to a pH of 7.5 using the process explained in Example 2. Using a medium-pressure chromatography system (MPLC), chloroform/ethanol/water=4/7/1.5 was used for the elution at a flow rate of 10 ml/min and a pressure of 2–5 bar. After a fore-run of 600 ml, 220 fractions each of 10 ml were collected, combining on the basis of the TLC. Besides mixed fractions containing MB, fractions 90–170 yielded 1.28 g of pure MB after evaporation, taking up in water and freeze-drying.

c) Purification of the Breakdown Product MC 2.2 g of polar crude product from the aqueous phase of the extraction were likewise chromatographed under pressure (MPLC). 500 g of silica gel with a pH of 7.5 were employed (process in Example 2), and the eluent used was ethyl acetate/i-propanol/water=4/5/5. The amount to be loaded was suspended in methanol with 15 g of silica gel, the solvent was evaporated off, and the support treated in this way was introduced into a precolumn, and then elution was carried out at a flow rate of 5 ml/min under a pressure of 2–4 bar. A fore-run of 940 ml was followed by fractionation in 250 fractions each of 10 ml. The fractions were tested by thin-layer chromatography in the system ethyl acetate/i-propanol/water=1/1/1 using PMS color reagent and detection of the UV absorption at 254 nm, and were combined. Besides mixed fractions, concentration of fractions 120–190 to the aqueous phase and subsequent freeze-drying revealed 1.3 g of pure MC, which was investigated by spectroscopy.

EXAMPLE 6

Elucidation of the Structures of the Products MA and MB obtained from Moenomycin A by Enzymatic Breakdown (The numbers of the structures relate to the formula diagram on page 19).

The structure deduced for MA was 1a. The assignment of the structure is based on the $^{13}C$ NMR spectrum of 1a. Reaction of 1a with diazomethane yielded the methyl ester 1b which is characterized by a $^1H$ NMR and an EI mass spectrum.

The structure deduced for MB on the basis of $^{13}C$ and FAB mass spectrum was 2. Hydrogenation of 2 yielded the decahydro derivative 3a which reacted with diazomethane to give 3b, which had already been obtained previously from moenomycin A by another route. It is consistent with the proposed structures that it was possible to convert 2 (MB) enzymatically into 1a (MA).

Description of the Experiments

1a:
$^{13}C$ NMR (100.6 MHz, CD$_3$OD): moenocinol moiety: $\delta = 67.5$ (C-1), 123.5 (C-2), 141.6 and 141.8 (C-3 and C-7), 32.3 and 32.5 (C-4 and C-5), 126.7 (c-6), 35.9 (C-8), 40.9 (C-9), 30.7 (C-10), 151.1 (C-11), 33.4 (C-12), 122.7 (C-13), 137.3 (C-14), 36.4 (C-15), 27.7 (C-16), 125.3 (C-17), 132.2 (C-18), 25.9 (C-19), 17.8 (C-20), 16.1 (C-21), 109.2 (C-22), 27.3 (C-23 and C-24), 23.8 (C-25).

Glyceric acid moiety: $\delta = 175.9$ (C-1), 80.6 (C-2), 64.1 (C-3).

$C_{28}H_{46}O_4$ (446.6).

1b:
1a was converted into the H$^+$ form in aqueous solution using ®Dowex 50 (H$^+$ form). 1a (H$^+$ form, 18.5 mg, 0.04 mmol) was dissolved in methanol (3 ml) and, at 0° C., excess ethereal diazomethane solution was added. The reaction mixture was maintained at 0° C. for 2 h and at 20° C. for 12 h and then evaporated to dryness. Column chromatography (5 g of SiO$_2$, petroleum ether/ethyl acetate 2:1) yielded 1b (3 mg).

$^1H$ NMR (80 MHz, CDCl$_3$): $\delta = 0.96$ (s, 6H, CH$_3$-23 and CH$_3$-24), 1.61 (s, 6H), 1.68 (s, 3H), 1.73 (s, 3H) (4×CH$_3$), 1.90–2.12 (allyl Hs), 2.62 (broad d, J=7Hz, CH$_2$-12), 3.78 (s, OCH$_3$), 3.60–4.30 (OCH$_2$ and OCH signals), 4.62 (broad s, CH$_2$-22), 4.87–5.47 (olefinic Hs).—C$_{29}$H$_{48}$O$_4$ (460.7), MS: m/z (%)=460 (0.03), 271 (10), 230 (19), 199 (68), 43 (100).

2:
$^{13}C$ NMR (100.6 MHz, D$_2$O): moenocinol moiety: $\delta = 68.6$ (C-1), 124.5 (C-2), 142.9 (C-3), 34.6 (C-4), 34.0 (C-5, C-10), 128.1 (C-6), 143.6 (C-7), 37.8 (C-8), 44.1 (C-9), 151.4 (C-11), 37.2 (C-12), 123.5 (C-13), 138.3 (C-14), 42.2 (C-15), 29.1 (C-16), 126.9 (C-17), 133.1 (C-18), 28.0 (C-19), 19.9 (C-20), 18.2 (C-21), 111.2 (C-22), 29.7 (C-23, 24), 25.9 (C-25). Glyceric acid moiety: $\delta = 179.0$ (C-1), 81.8 (C-2), 68.6 (C-3).—C$_{28}$H$_{47}$O$_7$P (526.7), FAB-MS (matrix: DMSO/glycerol): m/z=615 (M-3H+4Na)+, 593 (M-2H+3Na)+, 571 (M-H+2Na)+, 492, 267, 231, 185, 165, 143, 115.

3a:

(14.9 mg, 28.3 μmol) and PtO$_2$ (4 mg) were stirred in methanol (3 ml) and acetic acid (50 μl) in an H$_2$ atmosphere under normal conditions for 3 days. The catalyst was filtered off, and evaporation yielded 3a (13.5 mg). —C$_{28}$H$_{57}$O$_7$P (536.7), FAB-MS (matrix: DMSO/glycerol: m/z=625 (M-3H+4Na)+, 603 (M-2H+3Na)+, 581 (M-H+2Na)., 558 (M-H+Na)+,500, 498, 432, 404, 362, 340, 298, 288, 266, 186, 164, 142, 115, 93.

3b:

3a was treated in aqueous solution with the ion exchanger (Dowex 50, H+ form) in order to liberate all acidic groups. The resin was filtered off and then the solution was freeze-dried. 8.5 mg (15.9 μmol) of the sample treated in this way were dissolved in methanol (2 ml). An excess of ethereal diazomethane solution was added at 0° C. The mixture was left to stand at 0° C. for 2 h and at 20° C. for 12 h. Evaporation and column chromatography (5 g of SiO$_2$, petroleum ether/ethyl acetate 1:1) yielded 3b (4.0 mg).

$^1$H NMR (80 20 MHz, CDCl$_3$): δ=3.75 (s, OCH$_3$ and 2 d, 3J$_{H,P}$=10 and 12 Hz, P(OCH$_3$)$_2$), 3.20 4.40 (OCH$_2$ and OCH multiplets),—C$_{13}$H$_{63}$O$_7$P (578.8), MS: m/z (%)=563 (0.1, M-CH$_3$), 519 (1, M-COOCH$_3$), 452 (1, M-(CH$_3$O)$_2$P(O)OH), 381 (3, M-C$_{14}$H$_{29}$, breakage of the link between C-8 and C-9 of the 25 perhydromoenocinol moiety), 229 (8, a), 212 (6, b), 127 (20), 57 (100).

EXAMPLE 7

Antibiotic Activities of the Cleavage Products

An agar dilution test with Mueller-Hinton agar was carried out to determine the antibacterial activities (Antibiotics in Laboratory Medicine, V. Lorian, Ed., Baltimore 1986, pages 1-10).

| | Minimum inhibitory concentration (μg/ml) | | |
|---|---|---|---|
| Cleavage products | Str. pyogenes 77 | Staph. aureus 503 | E. coli DC2 |
| MA | >100 | >100 | >100 |
| MB | 3.125 | 25 | >100 |
| MC | >100 | >100 | >100 |

EXAMPLE 8

Transglycosylase Assay

The inhibition of the polymerization of the peptidoglycan-sugar chains by the cleavage products was carried out by the assay described by Izaki (J. Biol. Chem. 243, 3180-3192, 1968) using lipid intermediates from the cell membrane of E. coli K 12.

It emerges from this that moenomycin A (20 μg/ml) inhibits the transglycosylase reaction by 52.7% and the cleavage product MB inhibits the enzyme by 32.9%.

We claim:

1. Purified Moenomycinase having the following characteristics:
   (i) the ability to cleave phosphoglycolipid antibiotics at the phosphoglycosidic linkage;
   (ii) a pH optimum of 8.0 to 8.5;
   (iii) a temperature optimum of 45° to 55° C.;
   (iv) a $K_m$ value of 4 to 10 mmolar based on moenomycin A as substrate; and
   (v) a molecular weight of about 230,000±10,000 Dalton as determined by molecular sieve chromatography.

2. Moenomycinase as claimed in claim 1 produced by Bacillus spec. DSM 4675 and the variants and mutants thereof.

* * * * *